US008697929B2

(12) United States Patent
Ou et al.

(10) Patent No.: US 8,697,929 B2
(45) Date of Patent: Apr. 15, 2014

(54) XYLENE ISOMERIZATION PROCESS AND CATALYST THEREFOR

(75) Inventors: John Di-Yi Ou, Houston, TX (US); April D. Ross, Beaumont, TX (US); Doron Levin, Highland Park, NJ (US); Mohan Kalyanaraman, Media, PA (US); Wenyih Frank Lai, Bridgewater, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 238 days.

(21) Appl. No.: 13/081,351

(22) Filed: Apr. 6, 2011

(65) Prior Publication Data

US 2011/0263918 A1  Oct. 27, 2011

Related U.S. Application Data

(60) Provisional application No. 61/326,445, filed on Apr. 21, 2010.

(51) Int. Cl.
 *C07C 5/27* (2006.01)
(52) U.S. Cl.
 USPC .............. 585/481; 585/477; 585/480; 502/53
(58) Field of Classification Search
 CPC .. C07C 5/2729; C07C 5/2732; C07C 5/2737; C07C 15/08; B01J 29/40; B01J 29/7038; B01J 23/90; B01J 23/92; B01J 23/94; B01J 23/96; B01J 29/90; C10G 45/60; C10G 45/62; C10G 45/58; C10G 2400/30
 USPC ........ 585/477, 478, 480, 481; 502/53, 77, 71; 208/134, 141
 See application file for complete search history.

(56) References Cited

U.S. PATENT DOCUMENTS

| 3,856,871 | A | 12/1974 | Haag et al. |
| 4,482,773 | A | 11/1984 | Chu et al. |
| 4,508,836 | A | 4/1985 | Haag et al. |
| 4,980,046 | A | 12/1990 | Zarchy et al. |
| 5,877,374 | A | 3/1999 | Nacamuli et al. |
| 6,015,932 | A | 1/2000 | Frey |
| 6,180,550 | B1 | 1/2001 | Beck et al. |
| 6,355,853 | B1 * | 3/2002 | Sharma et al. ................. 585/481 |
| 6,448,459 | B1 | 9/2002 | Magne-Drisch et al. |
| 6,504,075 | B2 * | 1/2003 | Beck et al. ..................... 585/475 |
| 6,689,929 | B2 | 2/2004 | Williams et al. |

(Continued)

FOREIGN PATENT DOCUMENTS

| WO | WO 00/37398 | 6/2000 |
| WO | 2005/075389 | 8/2005 |
| WO | 2005/075390 | 8/2005 |
| WO | 2009/061303 | 5/2009 |

*Primary Examiner* — In Suk Bullock
*Assistant Examiner* — Candace R Chouinard
(74) *Attorney, Agent, or Firm* — Andrew B. Griffis

(57) ABSTRACT

The invention concerns a xylenes isomerization process for the production of equilibrium or near-equilibrium xylenes. The process utilizes a catalyst comprising HZSM-5 or MCM-49 and process conditions including a temperature of less than 295° C. and a pressure sufficient to maintain the xylenes in liquid phase. In embodiments, the process can be operated in a continuous mode with ppm levels of dissolved $H_2$ in the feed and in other embodiments in a cyclic mode without the $H_2$ in feed but with periodic regenerations using a feed having low ppm levels of $H_2$.

8 Claims, 3 Drawing Sheets

(56) References Cited

U.S. PATENT DOCUMENTS

| | | |
|---|---|---|
| 6,872,866 B1 | 3/2005 | Nemeth et al. |
| 6,878,855 B2 | 4/2005 | Deckman et al. |
| 7,244,409 B2 | 7/2007 | Burgfels et al. |
| 7,270,792 B2 * | 9/2007 | Deckman et al. ............ 422/236 |
| 7,371,913 B2 | 5/2008 | Bauer |
| 7,381,858 B2 * | 6/2008 | Huff et al. .................... 585/805 |
| 7,439,412 B2 | 10/2008 | Ou et al. |
| 7,495,137 B2 | 2/2009 | Zhou et al. |
| 7,569,136 B2 | 8/2009 | Ackerson et al. |
| 7,592,499 B2 | 9/2009 | Wolff et al. |
| 7,626,065 B2 | 12/2009 | Ou et al. |
| 2002/0082461 A1 | 6/2002 | Magne-Drisch et al. |
| 2005/0038308 A1 | 2/2005 | Wolff et al. |
| 2008/0159928 A1 | 7/2008 | Kokayeff et al. |
| 2009/0095651 A1 | 4/2009 | Leonard et al. |
| 2009/0182182 A1 | 7/2009 | Bauer |
| 2010/0152508 A1 | 6/2010 | Ou et al. |

\* cited by examiner

XYLENE ISOMERIZATION PROCESS AND CATALYST THEREFOR

PRIORITY CLAIM

This application claims the benefit of U.S. Provisional Application No. 61/326,445 filed Apr. 21, 2010, the disclosure of which is incorporated herein by reference in its entirety.

FIELD OF THE INVENTION

The invention relates to a xylene isomerization process and catalyst therefor.

BACKGROUND OF THE INVENTION

An equilibrium mixture of xylenes contains about 24% para-xylene (PX), 56% meta-xylene (MX), and 20% ortho-xylene (OX). PX is relatively high value as compared with MX and OX, and it is desirable to isomerize OX and/or MX to PX, such as isomerizing a PX-lean stream to equilibrium for PX recovery. It is an active area of research.

Typically xylene streams found in chemical or petrochemical plants also contain ethylbenzene (EB). Conventional isomerization technologies operating at high temperatures (e.g.: 400° C.) in vapor phase isomerize the xylenes and dealkylate EB to benzene. Other vapor-phase isomerization technologies convert EB to xylenes in addition to xylenes isomerization. There are also liquid-phase isomerization technologies. Conventional isomerization technologies typically produce significant amounts (>0.5 mol %) of byproducts such as benzene and A9+ (aromatic hydrocarbons having 9 or more carbon atoms). Thus, it is necessary to install a topping and/or a tailing distillation column to reduce the byproducts concentrations. In many situations, installing new distillation columns would not be feasible due to economic and/or physical constraints. Most isomerization technologies also require high hydrogen partial pressure to maintain the catalyst activity, which makes the process arrangement complex and expensive.

U.S. Pat. No. 6,180,550 teaches ZSM-5 useful in the liquid phase isomerization of xylene. The zeolite used has a SiO2/Al2O3 ratio of less than 20.

U.S. Pat. No. 6,448,459 teaches isomerization without hydrogen in a liquid phase diluted with toluene used as desorbent in a simulated moving bed adsorptive separation unit. The catalyst used in the liquid phase isomerization is said to be zeolitic, for example ZSM-5, and in the example it is specified that there is no hydrogen.

U.S. Pat. No. 6,872,866 teaches a two stage, liquid or partially liquid phase isomerization process using a zeolitic-based catalyst system preferably based on zeolite beta and on pentasil-type zeolite. This patent also sets forth numerous examples of prior art catalyst systems, including ZSM-5.

U.S. Pat. No. 7,244,409 teaches small crystallite ZSM-5 which may be used for isomerization reactions.

U.S. Pat. No. 7,371,913 teaches a ZSM-5 mole sieve further comprising Ga is used as an isomerization catalyst to provide an increased amount of PX in the liquid phase in the substantial absence of $H_2$. The amount of $H_2$ present is stated to be less than 0.05, preferably less than 0.01, mole $H_2$/mole feed.

U.S. Pat. No. 7,495,137 teaches a two-stage isomerization system, the first zone operating in the absence of hydrogen (as in the above patent) using a platinum-free catalyst and the second zone using a catalyst comprising a molecular sieve and a platinum-group metal component. The catalyst in the first zone is preferably a Ga-MFI-type zeolite and it is preferred that the catalyst for the first zone has a Si:Al ratio greater than about 10.

U.S. Pat. No. 7,592,499 teaches a multi-stage process for co-producing PX and styrene from a feed of hydrocarbons comprising xylenes and EB. In the first stage, PX is separated from the feed by means of a simulated moving bed adsorptive separation column to produce a raffinate comprising EB, OX, and MX. Next, EB in the raffinate is dehydrogenated to styrene. Eventually a stream containing unconverted EB, MX, and OX is obtained and contacted with an isomerization catalyst to preferably in the liquid phase. The catalyst is zeolitic, such as ZSM-5.

U.S. 2009-0182182 teaches a two-stage isomerization process, the first stage in the liquid phase in the substantial absence of $H_2$ to obtain an intermediate stream. In the second stage, the intermediate stream is mixed with a stream rich in naphthene, and contacted with an isomerization catalyst. By "substantial absence of $H_2$," is meant no free hydrogen is added to a feed mixture and any dissolved hydrogen from prior processing is substantially less than about 0.05 moles/mole of feed. The first isomerization catalyst includes a molecular sieve, typically an aluminosilicate having a $Si:Al_2$ ratio greater than about 10. In the example given, a Ga source is used to make the catalysts for both the first and second isomerization steps.

U.S. Publication No. 2010-0152508 teaches a process for isomerization that is at least partially in the liquid phase and includes a step of removal of C9 aromatic hydrocarbons from a feedstream including C8 and C9 aromatic hydrocarbons.

The present inventors have discovered a xylenes isomerization technology to provide a product enriched in PX when compared with the feedstream to the process. In embodiments the process takes a PX-lean feedstream to produce a product having equilibrium or near equilibrium xylenes. In embodiments the process produces very low level of by-products (such as <0.3 wt. %). Thus there is no need for additional distillation columns. Furthermore, the technology can operate without the presence of any hydrogen or with only low ppm levels of dissolved hydrogen, making it a simple and cost-effective process.

SUMMARY OF THE INVENTION

The invention is directed to a xylenes isomerization process, including a liquid phase isomerization, for the production of equilibrium or near-equilibrium xylenes, wherein the process conditions include a temperature of less than 295° C. and a pressure sufficient to maintain the xylenes in liquid phase.

In embodiments, the liquid phase isomerization process utilizes a catalyst comprising ZSM-5 and/or MCM-49.

In embodiments, the process can be operated in a continuous mode with low ppm levels of $H_2$ in the feed and in other embodiments in a cyclic mode without $H_2$ in feed but with periodic regenerations.

In embodiments, the process is operated in a continuous mode with from 4 to 10 ppm $H_2$ at a temperature of less than 295° C. and total pressure sufficient to maintain the xylenes in the liquid phase.

In embodiments, the process is operated in a cyclic mode without $H_2$ in the feed but with periodic regenerations using greater than 5 ppm $H_2$ in the feed, in embodiments at least 10 ppm $H_2$ in the feed, in other embodiments at least 20 ppm $H_2$ in the feed.

It is an object of the invention to provide a xylene isomerization process including a liquid phase isomerization process which, compared to conventional xylenes isomerization processes, provides at least one of the advantages selected from low investment, low operating costs, low byproduct yields, and low xylene loss.

It is another object of the invention to provide a liquid phase xylene isomerization process that uses at most only low ppm levels of hydrogen and that in embodiments can be regenerated numerous times by a very simple in situ procedure.

These and other objects, features, and advantages will become apparent as reference is made to the following detailed description, preferred embodiments, examples, and appended claims.

DETAILED DESCRIPTION

Figure 1A:
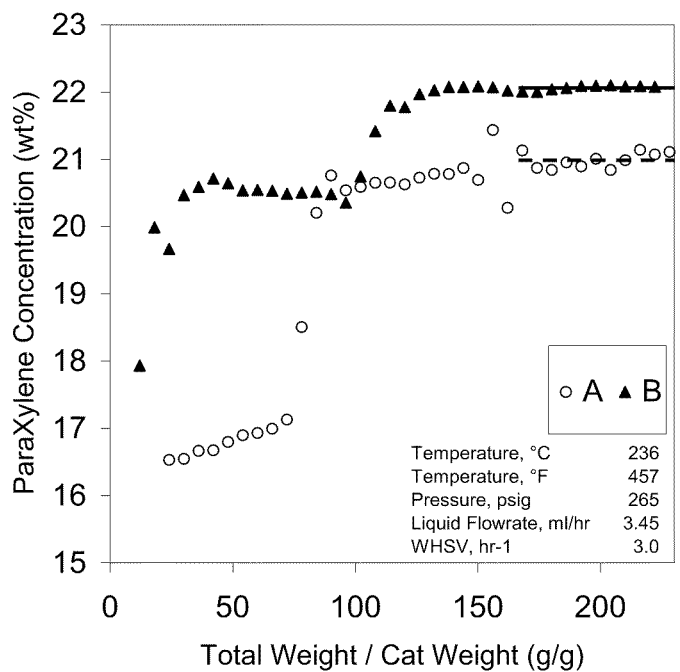
FIGS. 1A and 1B illustrate catalytic activities of ZSM-5 and MCM-49 zeolites for embodiments of the liquid phase xylene isomerization process according to the invention.

According to the invention, there is provided a process for the isomerization of xylenes including the liquid phase isomerization of xylenes at a temperature of less than 295° C. and a pressure sufficient to maintain the xylenes in liquid phase.

In embodiments, the process utilizes a catalyst comprising a zeolite, preferably at least one selected from the group consisting of ZSM-5 and MCM-49.

In embodiments, the process utilizes a catalyst comprising ZSM-5 along with a binder or the ZSM-5 may be self-bound.

In preferred embodiments the catalyst is characterized by one or more of the following characteristics:
the ZSM-5 is in the proton form (HZSM-5);
the ZSM-5 has a crystal size of less than 0.1 microns;
the ZSM-5 has a mesoporous surface area (MSA) greater than 45 $m^2/g$;
the ZSM-5 has a zeolite surface area (ZSA) to mesoporous surface area (MSA) ratio of less than 9;
a silica to alumina weight ratio in the range of 20 to 50.

As used herein, "crystal size" means average crystal size and is conveniently determined by electron microscopy, as is well-known per se in the art. The surface areas may also be determined by methods well-known in the art.

The catalyst can be formulated using various techniques such as extrusion, pelletization, oil dropping, spray drying, and the like, techniques which are per se well-known in the art. Optionally, binder materials such as alumina, silica, clay, aluminosilicate, may be used in the formulation. In preferred embodiments, the catalyst is characterized by one or more of the following properties with respect to the binder:
the zeolite:binder weight ratio is from 1:9 to 9:1;
the binder preferably comprises silica, alumina, and aluminosilicate;
the catalyst is preferably extruded using acetic acid as extrusion aid.

The preferred reactor is fixed bed and the flow may be up or down.

In embodiments, the process can be operated in a continuous mode with low ppm levels of $H_2$ dissolved in the feed and in other embodiments in a cyclic mode without the $H_2$ in feed but with periodic regenerations.

By "low ppm" is meant levels which one of ordinary skill in the art would express as "ppm", generally below 100 ppm. The expression "ppm" is weight ppm (wppm) unless otherwise specified.

In embodiments, very low level of by products are produced, such as less than 1 wt % or preferably less than 0.5 wt % of by products selected from non-aromatic compounds, benzene and A9+ (aromatic hydrocarbons having 9 or more carbon atoms), and mixtures thereof.

The process comprises contacting a feedstream comprising C8 aromatic hydrocarbons with a catalyst suitable for isomerization, preferably a catalyst comprising MCM-49 and/or ZSM-5, preferably a catalyst comprising ZSM-5 and more preferably having one or more of the aforementioned properties and most preferably all of the aforementioned properties, at a temperature below 295° C., preferably below 280° C., and at a pressure sufficiently to keep the reactant in liquid phase. One of skill in the art in the possession of the present disclosure would be able to determine other operating characteristics, such as a lower temperature, within which the present invention may be practice. Lower limits may be, for instance, above 180° C. or 190° C. or 200° C., or 210° C., and the like. The flow rate can be selected by one of ordinary skill in the art in possession of the present disclosure, but may advantageously be selected within the range from 1 to 100 WHSV, preferably from 1 to 20 WHSV, and more preferably from 1 to 10 WHSV.

The following examples are intended to exemplify the invention and are not intended to be limiting.

In an embodiment, a PX-lean xylenes feedstream is fed to at least one reactor. "PX-lean", for the purposes of the present invention, means less than equilibrium amount of paraxylene, i.e., less than 24 mol % PX, based on 100 mol % xylene feedstream. In preferred embodiments, the feedstream will comprise from 2 to 18 mol % PX, based on 100 mol % xylene feedstream.

In preferred embodiments, there is no $H_2$ in the xylene feedstream. It is difficult to measure $H_2$ in xylene feedstreams with any accuracy at low ppm levels (which may be attempted by such methods as GC techniques commonly known), and therefore the expression "no $H_2$" as used herein is meant no $H_2$ beyond inevitable impurities, and also that there is no purposeful addition of $H_2$ in such feedstreams. The feedstreams may also be purged with an inert gas, such as $N_2$, to lower $H_2$ levels from "inevitable impurities" if so desired. The expression "$H_2$-free", also used herein, is intended to mean the same thing as "no $H_2$". In embodiments, it will be sufficient for the purposes of the present invention that the "$H_2$-free" feedstream contain less than or equal to 4 ppm $H_2$. Low ppm amounts of $H_2$ used in the continuous mode will be, preferably, greater than 4 ppm to about 10 ppm (equivalent to 0.00001 moles of $H_2$ per mole of xylenes). However, the amount of $H_2$ may be higher, such as 50 or 100 ppm.

In practice, one way of accomplishing low ppm levels of $H_2$ is by controlling the quantity of $H_2$ added to the "$H_2$-free stream". For instance, we may know that a stream is $H_2$ free because we know what upstream processing it has gone through, such as distillation which would rid a stream of H2 easily. Then by carefully controlling how much $H_2$ is added, we would know the final $H_2$ quantity.

The reactor may be of any type, such as a fixed bed reactor, fluid bed reactor, dense bed reactor, and the like. For example, the reactor could be a tubular fixed bed reactor packed with a catalyst suitable for isomerization of C8 aromatic hydrocarbons, more preferably a catalyst comprising HZSM-5 or MCM-49. The feedstream can flow through the reactor in either up-flow or down-flow mode. Such a reactor can be operated at a temperature below 295° C., a flow rate within the range of 0.1 to 100 WHSV (Weight Hourly Space Velocity), and a pressure sufficiently high to keep the feedstream at liquid phase inside the reactor and advantageously maintained so as to achieve the low byproducts yields. The person of ordinary skill in the art, in possession of the present disclosure, can achieve such conditions without more than routine experimentation. Once temperature is set, those skilled in the art can determine what pressure to use to keep it in liquid phase based on xylenes VLE (vapor-liquid-equilibrium) data. By way of example, without intending to be limiting, in embodiments the pressure may be above 100 psia, or preferably above 150 psia.

Depending on the operating conditions, the catalyst may exhibit a slow deactivation. It has been also unexpectedly discovered by the present inventors that low ppm levels of dissolved hydrogen in the xylenes feed can completely mitigate such deactivation. Thus one can run the reactor with a $H_2$-free xylene feed for a period of time, the length of which depends on the selection of operating parameters of the operator, and at the end of the operation, replace the $H_2$-free xylene feed with a $H_2$-containing xylene feed at the same operating conditions. Thus, in this embodiment, $H_2$ is now purposefully added to the feed. Only low ppm levels are necessary. Although, as mentioned above, GC techniques are not particularly good at measuring $H_2$ levels accurately at low ppm levels in a C8 aromatic hydrocarbon feedstream, the presence of $H_2$ at such levels can be estimated based on $H_2$-xylenes VLE. For the purposes of the present invention, when the "$H_2$-free" feedstream is defined as containing 0.00005 moles $H_2$/mole xylenes or less, or 0.00001 moles $H_2$/mole xylenes or less, the $H_2$-containing xylene feed should have greater than 0.00005 moles $H_2$/mole xylenes, or greater than 0.00001 moles $H_2$/mole xylenes, respectively.

It has been surprisingly found that the $H_2$-containing xylene feed will regenerate the catalyst to recover the lost activity. The regeneration period can vary, such as from 1 day to a few weeks. At the end of the regeneration, an operator can replace the $H_2$-containing feed with the $H_2$-free feed and resume the normal operation.

This regeneration technique has at least several advantages. It is easy to implement and cost effective. Hydrogen can readily dissolve in xylenes at the required level. By way of example, at 160 psia, 71 ppm $H_2$ will be dissolved in xylenes at room temperature. It does not require such expensive and complex process equipment as separator and recompressor that is required for the high $H_2$ partial pressure in conventional vapor-phase isomerization technologies. The regeneration is done with a $H_2$-containing xylene feed at the same conditions as that for the normal operation, which means that even during regeneration, the reactor is still producing equilibrium or near equilibrium xylenes; thus would be no productivity loss. In embodiments the operator can increase the $H_2$ concentration during the regeneration to as high as 100% $H_2$ and 0% xylenes and still accomplish the objective.

In another embodiment, low ppm levels of $H_2$ such as 4 to 100 ppm, preferably 4 to 10 ppm (within the standard sampling error possible by current measurement techniques) are dissolved in the xylene feed and fed to the reactor continuously through out the operation. The $H_2$ at such levels will completely prevent the catalyst deactivation. As a result, in this embodiment, there is provided a process allowing for long, continuous operation without any need to stop for regeneration. In addition to the advantages listed above, in this embodiment a consistently high PX yield is possible at all times.

In order to better understand the invention, reference will now be made to specific examples, which are intended to merely be representative of the present invention and should not be taken as limiting.

Example 1

A sample of 1/16" extruded H-ZSM-5 catalyst, obtained from PQ Corporation, having a silica/alumina ratio of 30, was ground to 30/60 mesh and packed in an 0.180"ID×0.625" length tubular reactor to a level of 0.13 gram. The catalyst was then dried under flowing nitrogen gas at 200° C. for 10 hours to remove moisture. Afterward, the catalyst was contacted with xylenes feed, first without dissolved $H_2$ ($H_2$-free according to the present invention), and then with $H_2$ dissolved in the feed to a level of 130 ppm by weight. Isomerization conditions were set at 280 psia, 232° C. and 3 WHSV. Under these conditions, the xylenes feed was isomerized and the rate of catalyst deactivation or regeneration was calculated based on product analysis.

Results, as shown in the Table 1, demonstrate that the presence of dissolved hydrogen not only stopped catalyst deactivation but also restored and maintain the catalyst activity.

TABLE 1

| Xylene Feed | without dissolved $H_2$ | with dissolved $H_2$ |
|---|---|---|
| Change in PX yield (wt %) | −1.0 | +0.7 |
| Cumulative bed weights of feed (g of feed/g of catalyst) | 0-1996 | 1996-3910 |
| Rate of deactivation (ΔPX wt %/bed weights) | −5.0 × 10⁻⁴ | |
| Rate of restoration (ΔPX wt %/bed weights) | | +4.0 × 10⁻⁴ |

Additional experiments were performed in order to identify the scope of the present invention, wherein a PX-lean feedstream is isomerized to equilibrium while minimizing byproduct formation.

Preliminary experiments were performed on ZSM-5 zeolites with varying properties and on a MCM-49 zeolite as listed in Table 2.

TABLE 2

| Crystal | Crystal Type | SiO2/Al2O3 Ratios | Crystal Sizes, micron |
|---|---|---|---|
| I | ZSM-5 | 25 | 0.5 |
| II | ZSM-5 | 60 | <0.1 |
| III | ZSM-5 | 25 | <0.1 |
| IV | MCM-49 | | |

Example 2

This Example illustrates that the unexpected findings with respect to the process of the invention may be achieved by catalysts other catalysts.

Figure 1B:
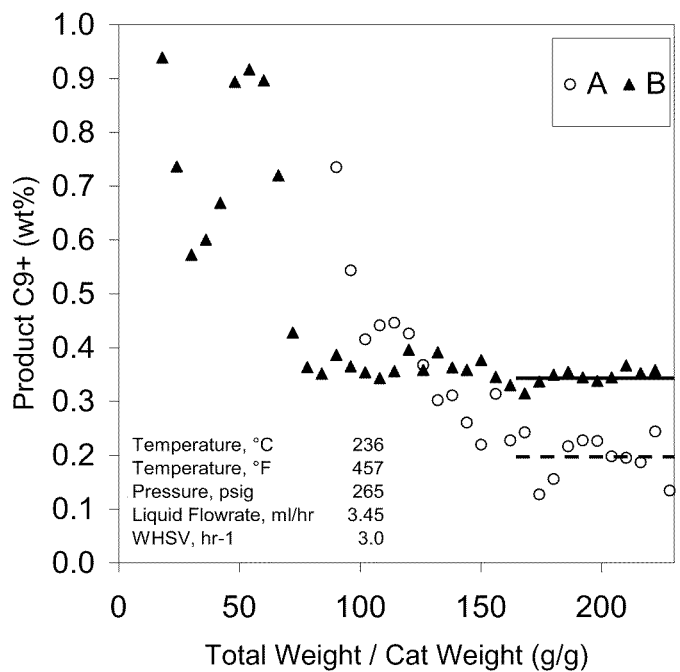

MCM49 and ZSM5 zeolites (shown in Table 3) were tested for liquid phase xylene isomerization according to the invention. The feeds used are shown in Table 4, with results shown in FIG. 1. Both zeolites isomerized xylenes to para-xylenes at 236° C., 3 weighted hourly space velocity (1 gram of catalyst used), and 265 psig. MCM49 had a higher para-xylene yield but also higher by-products as indicated by the product C9+ content, also shown in FIG. 1. Thus, one could choose either zeolite for liquid phase xylene isomerization on a case-by-case basis.

TABLE 3

| Catalyst | Crystal | Form Tested | Finishing |
|---|---|---|---|
| A | III | powder | Exchanged and Calcined for 6 hours at 1000 F. |
| B | IV | Self-Bound 1/16" Quadrulobe (extruded with PVA) | Exchanged and Calcined for 8 hours at 1000 F. |

TABLE 4

| Feed Component | Feed wt % for Catalyst A | Feed wt % for Catalyst B |
|---|---|---|
| Methylcyclohexane | 0.84 | 0.01 |
| DiMethylcyclohexane | 1.93 | 4.10 |
| Benzene | 0.00 | 0.005 |
| Toluene | 1.32 | 1.00 |
| Ethylbenzene | 2.86 | 3.06 |
| Para Xylene | 13.36 | 12.80 |
| Meta Xylene | 62.90 | 62.26 |
| Ortho Xylene | 16.77 | 16.75 |
| Cumene | 0.02 | 0.02 |
| Other C9+ | 0.01 | 0.01 |

Example 3

The present inventors have also discovered that silica/alumina ratio and crystal size of the HZSM-5 zeolite are important factors to the catalyst performance. Thus for liquid phase xylenes isomerization according to the present invention, a catalyst based on a HZSM-5 zeolite with silica/alumina ratio of 30 or less and crystal size less than 0.1 micron provides even more advantageous liquid phase xylenes isomerization performance, superior to that of the catalysts with ZSM-5 zeolites having silica/alumina ratios and crystal sizes outside the specified ranges.

Three ZSM-5 extrudates were prepared using 3 different ZSM5 crystals and are shown in Table 5. The crystals were ion exchanged to proton form and extruded into 1/20" quadrulobes extrudates with an alumina binder and 1% acetic acid as an extrusion aide. The weight ratio of crystal to binder was 4. The extrudates were calcined at 1000° F.

TABLE 5

| Catalyst | Crystal | Catalyst loading, g | Reactor temp. ° C. | Reactor pressure, psig | Flowrate, Weight Hourly Space Velocity |
|---|---|---|---|---|---|
| C | I | 0.4550 | 246 | 265 | 3.69 |
| D | II | 0.4545 | 246 | 265 | 3.69 |
| E | III | 0.4610 | 246 | 265 | 3.74 |

The extrudates were evaluated using a feed of 13.28% para-xylene, 63.72% meta-xylene, 17.94% ortho-xylene, 1.52% ethylbenzene, 1.28% toluene, and 2.25% non-aromatics, and low levels of benzene and nine-carbon aromatic compounds. The tests were performed in a 1/4" stainless steel reactor with the feed going up flow through the catalyst bed. Test conditions are listed in Table 4.

Figure 2:
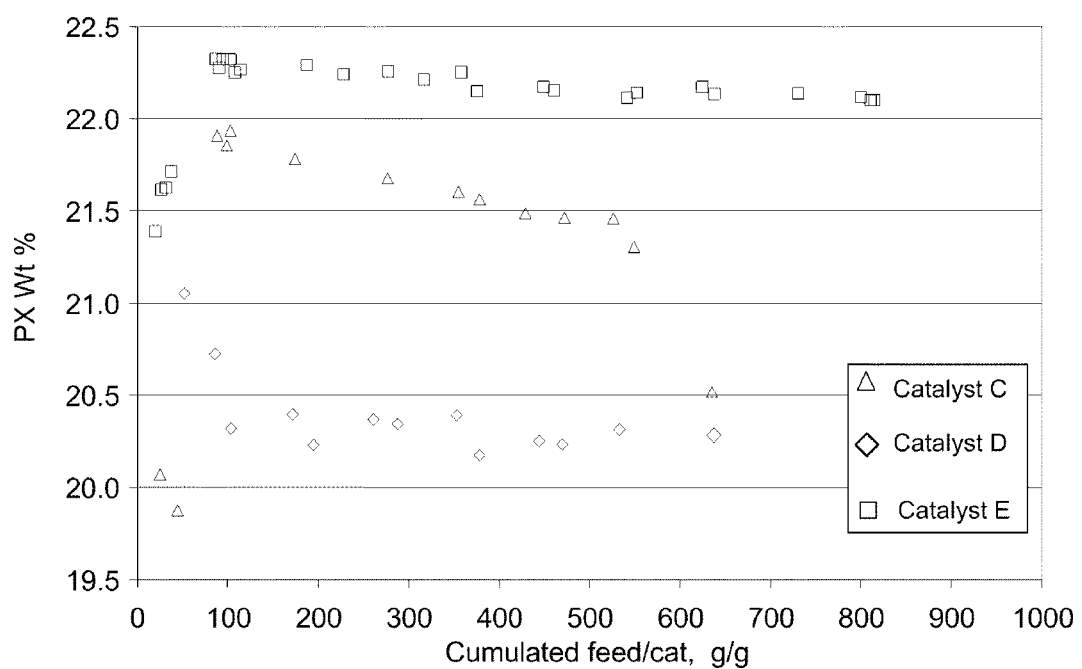
FIG. 2 illustrate the effect of a ZSM-5 zeolite's crystal size and silica/alumina ratio for an embodiment of the liquid phase xylene isomerization process according to the invention.

Test results are shown in FIG. 2. It is seen that all three catalysts were able to isomerize meta- and ortho-xylene to para-xylene. However, the PX yield decreased in the order of E>C>D and that the catalyst with crystal III delivered a near-equilibrium para-xylene yield (97-98% equilibrium). A comparison between Catalysts E and D shows that lowering silica/alumina ratio from 60 to 25 raised para-xylene yield from about 20.2% to about 22.2% and between Catalysts E and C shows that reducing crystal size from 0.5 to <0.1 micron raised para-xylene yield from an average of 21.6% to 22.2%.

Examples 4-6

In preparing formed extrudates, higher ratios of zeolite to binder proved to more efficiently isomerize the xylenes to para-xylene.

Three ZSM-5 extrudates were prepared all using crystal III (described in Table 2) and are shown in Table 6. The crystals were ion exchanged to proton form and extruded into 1/20" quadrulobes extrudates with an alumina binder. Catalyst H was also extruded using 1% acetic acid as an extrusion aide to improve crush strength. All extrudates were calcined at 1000° F. (about 538° C.).

TABLE 6

| Catalyst | Crystal | Zeolite:Binder |
|---|---|---|
| F | III | 65:35 |
| G | III | 75:25 |
| H | III | 80:20 |

The extrudates were evaluated using a feed shown in Table 7. One gram of each catalyst was used in the testing. The pressure was 265 psig for all runs and the feed was $H_2$-free PX-lean xylenes.

TABLE 7

| Feed Component | Wt % |
|---|---|
| C8 non-Aromatics | 4.31 |
| Benzene | 0.004 |
| Toluene | 0.99 |
| Ethylbenzene | 3.07 |
| Para Xylene | 12.79 |
| Meta Xylene | 62.1 |
| Ortho Xylene | 16.71 |
| C9 | 0.01 |
| C10+ | 0.02 |

Figure 3:
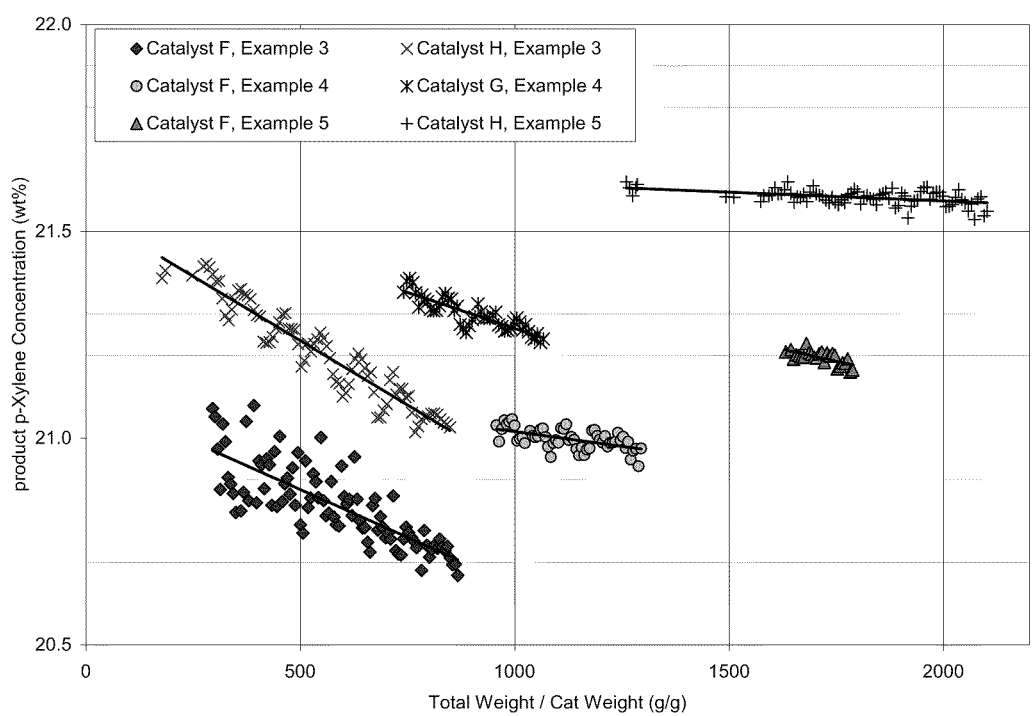
FIG. 3 illustrate the effect of an extrudate's zeolite content for an embodiment of the liquid phase xylene isomerization process according to the invention.

Test results are shown in FIG. 3 and Table 8. For Example 3, catalysts F and H were both tested at 246° C. and WHSV based on only the zeolite of 4.6. Overall WHSVs were 3.0 for Catalyst F and 3.7 for Catalyst H. Despite the higher overall WHSV, Catalyst H yielded higher para-xylene concentration in the product. This trend was also observed in Examples 5 and 6. Therefore, increasing the zeolite concentration in the formed extrudate makes the zeolite more effective.

TABLE 8

| | Catalyst | Temp., C. | Overall WHSV, 1/hr | Zeolite WHSV, 1/h | Cumulative Feed/Catalyst (g/g) | p-Xylene product concentration (wt %) |
|---|---|---|---|---|---|---|
| Example 3 | F | 246 | 3.0 | 4.6 | 500 | 20.9 |
| | H | 246 | 3.7 | 4.6 | 500 | 21.2 |
| Example 4 | F | 250 | 3.0 | 4.6 | 1000 | 21.0 |
| | G | 250 | 3.5 | 4.67 | 1000 | 21.3 |
| Example 5 | F | 254 | 3.0 | 4.6 | 1700 | 21.2 |
| | H | 255 | 3.7 | 4.6 | 1700 | 21.6 |

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process comprising contacting a feedstream including C8 aromatic hydrocarbons, said feedstream characterized by having 4 to 100 ppm levels of dissolved $H_2$, wherein said feedstream is further characterized as paraxylene-lean relative to the equilibrium amount of paraxylene in xylenes, with a catalyst suitable for isomerization of xylenes, in a reactor under conditions including a temperature of less than 295° C., and a pressure sufficient to maintain the xylenes in liquid phase, and isomerizing said xylenes in the liquid phase to obtain a product stream having an increased concentration of paraxylene relative to the concentration of paraxylene in said feedstream, wherein said catalyst comprises at least one of HZSM-5 and MCM-49, wherein said HZSM-5 is characterized by the following characteristics:
   an average crystal size of less than 0.1 microns;
   a mesoporous surface area (MSA) greater than 45 $m^2/g$;
   a zeolite surface area (ZSA) to mesoporous surface area (MSA) ratio of less than 9;
   a silica/alumina ratio of 20 to 50 by weight;
   wherein said process is then operated in a cyclic mode with a feedstream comprising less than 4 ppm dissolved $H_2$, and further wherein said catalyst is periodically regenerated by a step including contacting said catalyst with an $H_2$-containing feedstream.

2. The process according to claim 1, wherein said reactor temperature is less than 280° C.

3. The process of claim 1, wherein said reactor is selected from a fixed bed reactor, a fluid bed reactor, a dense bed reactor, and a simulated moving bed reactor.

4. The process of claim 3, wherein said feedstream contacts said catalyst at a flow rate of 1 to 10 WHSV.

5. The process of claim 3, wherein said contacting is conducted with an up-flow mode of operation.

6. The process of claim 3, wherein said contacting is conducted with a down-flow mode of operation.

7. The process of claim 1, wherein said catalyst comprises 10 wt %-90 wt % of HZSM-5 zeolite.

8. The process of claim 1, wherein said catalyst comprises HZSM-5 formed by extrusion, using acetic acid as an extrusion aid.

* * * * *